United States Patent [19]

Kabra et al.

[11] Patent Number: 5,618,800
[45] Date of Patent: Apr. 8, 1997

[54] THERMALLY-GELLING DRUG DELIVERY VEHICLES CONTAINING CELLULOSE ETHERS

[75] Inventors: Bhagwati P. Kabra, Fort Worth; John C. Lang, Arlington, both of Tex.

[73] Assignee: Alcon Laboratories, Inc., Fort Worth, Tex.

[21] Appl. No.: 518,289

[22] Filed: Aug. 23, 1995

Related U.S. Application Data

[63] Continuation-in-part of Ser. No. 298,244, Aug. 30, 1994, abandoned.

[51] Int. Cl.$^6$ .......................... A61K 31/715; C08B 11/02; C08B 11/08

[52] U.S. Cl. .......................... 514/57; 514/912; 514/913; 514/914; 536/84

[58] Field of Search .......................... 514/57, 912, 913, 514/914, 915; 424/427; 536/84

[56] References Cited

U.S. PATENT DOCUMENTS

| | | | |
|---|---|---|---|
| 3,767,788 | 10/1973 | Rankin | 424/78 |
| 3,856,919 | 12/1974 | Rankin | 424/78 |
| 3,926,951 | 11/1975 | Lindenfors et al. | 536/91 |
| 3,947,573 | 3/1976 | Rankin | 424/80 |
| 4,001,211 | 1/1977 | Sarkar | 536/84 |
| 4,136,173 | 1/1979 | Pramoda et al. | 424/177 |
| 4,136,177 | 1/1979 | Lin et al. | 424/211 |
| 4,136,178 | 1/1979 | Lin et al. | 424/211 |
| 4,188,373 | 2/1980 | Krezanoski | 424/78 |
| 4,474,751 | 10/1984 | Haslam et al. | 424/78 |
| 4,474,752 | 10/1984 | Haslam et al. | 424/78 |
| 4,861,760 | 8/1989 | Mazuel et al. | 514/54 |
| 5,077,033 | 12/1991 | Viegas et al. | 514/668 |
| 5,124,151 | 6/1992 | Viegas et al. | 424/422 |
| 5,126,141 | 6/1992 | Henry | 424/423 |
| 5,143,731 | 9/1992 | Viegas et al. | 424/486 |
| 5,212,162 | 5/1993 | Missel et al. | 514/54 |
| 5,252,318 | 10/1993 | Joshi et al. | 424/78.04 |
| 5,279,660 | 1/1994 | Carlsson et al. | 106/197.1 |
| 5,296,228 | 3/1994 | Chang et al. | 424/422 |
| 5,306,501 | 4/1994 | Viegas et al. | 424/423 |
| 5,318,780 | 6/1994 | Viegas et al. | 424/427 |
| 5,358,706 | 10/1994 | Marlin et al. | 424/78.04 |
| 5,470,881 | 11/1995 | Charlton et al. | 514/912 |

FOREIGN PATENT DOCUMENTS

| | | |
|---|---|---|
| 0277494B1 | 7/1987 | European Pat. Off. |
| WO94/23750 | 10/1994 | Japan |
| WO89/11503 | 11/1989 | WIPO |
| WO92/09307 | 6/1992 | WIPO |

OTHER PUBLICATIONS

Carlsson et al., "Thermal Gelation of Nonionic Cellulose Ethers and Iionic Surfactants in Water," *Colloids and Surfaces*, vol. 47, 147–165 (1990).

Greminger, Jr. et al., "Methylcellulose and its Derivatives," *Industrial Gums*, Academic Press, New York, Chapter XXVIII, 619–647 (1973).

Jullander, "Water Solubility of Ethyl Cellulose," *Acta Chemica Scandinavica*, 1291–1295 (1955).

Sarkar, "Thermal Gelation Properties of Methyl and Hydroxypropyl Methylcellulose," *J. of Applied Polymer Science*, vol. 24, 1073–1087 (1979).

*Primary Examiner*—John Kight
*Assistant Examiner*—Everett White
*Attorney, Agent, or Firm*—Patrick M. Ryan

[57] ABSTRACT

Drug delivery vehicles which reversibly increase in either loss modulus or storage modulus, or both, upon contact with the eye, skin, mucous membrane or body cavity are disclosed. The vehicles contain one or more nonionic substituted cellulose ethers and do not require a charged surfactant or a pH-sensitive polymer for such increase in loss modulus or storage modulus, or both, upon administration. In one embodiment, the vehicles gel upon instillation in the eye.

39 Claims, No Drawings

5,618,800

1

THERMALLY-GELLING DRUG DELIVERY VEHICLES CONTAINING CELLULOSE ETHERS

This application is a continuation-in-part of U.S. Ser. No. 08/298,244, filed on Aug. 30, 1994, now abandoned.

BACKGROUND OF THE INVENTION

1. Field of the Invention

The present invention relates to pharmaceutical drug delivery vehicles. In particular, this invention relates to drug delivery vehicles which can be administrable as a drop, and which reversibly increase in loss modulus, storage modulus, or both, upon contact with the eye, skin, mucous membrane or a body cavity.

2. Description of Related Art

A variety of gelling drug delivery systems have been developed in an effort to prolong the contact or residence time of pharmaceutical drugs at target sites on or within the body. Drug delivery vehicles containing polysaccharide polymers which gel in response to a pH change have been proposed, such as those described in U.S. Pat. Nos. 4,136,173, 4,136,177, and 4,136,178, for example. However, compositions having an initial pH which is too low are irritating when administered to sensitive parts of the body, such as the eye.

Alternatively, drug delivery systems which gel in response to changes in ionic strength have been proposed, such as those described in European Patent No. 0 227 494 B1 and U.S. Pat. No. 4,861,760. The rates of gelation for systems which gel in response to ionic changes are dependant on the supply and diffusion of ions, and consequently are generally slower than those for thermally gelling systems because the diffusion of ions is generally a slower process than heat transfer. In addition, certain charged drug compounds cannot be used in drug delivery systems which gel in response to changes in ionic strength because they may cause premature gelation.

U.S. Pat. No. 5,212,162 discloses compositions containing both a gelling polysaccharide and a drug carrier substrate, such as finely-divided solids, colloidal particles, or soluble polymers and/or polyelectrolytes which are capable of selective adsorption or binding with drug molecules. The polysaccharide is capable of reversibly gelling based on a change in ionic strength or pH. Such factors as a change in temperature, amount and type of drug carrier substrate, and characteristics and concentrations of drugs or other adjuvants may also affect the ability of the polysaccharide to undergo a liquid-to-gel transition. The preferred polysaccharides are carrageenans.

Drug delivery systems which gel in response to temperature changes have also been proposed. For example, drug delivery systems utilizing Tetronic®, Pluronic®, or other polyols have been disclosed in U.S. Pat. Nos. 4,474,751; 4,474,752; and 4,188,373. U.S. Pat. Nos. 5,124,151; and 5,306,501 also disclose thermally gelling systems. Several disadvantages are associated with these materials. One disadvantage common to all of these thermally gelling systems is that they require a large amount of polymer (10–50 wt. %), and such large amounts of polymer can be irritating and/or toxic to the eye. Another disadvantage of some of the known thermally gelling systems is that they gel irreversibly. Such thermally irreversible gels require special precautions for product shipping and handling.

2

It is an inherent requirement that drug delivery systems which gel solely in response to temperature changes undergo the "sol-gel" transition at temperatures lower than physiologic temperature. It is known that methylcellulose and its hydroxyalkyl derivatives reversibly gel with increases in temperature. Generally, however, the liquid-to-gel transition temperature for cellulose polysaccharides, such as methylcellulose, occurs at temperatures well above physiologic temperature. See, for example, N. Sarkar, "Thermal Gelation Properties of Methyl and Hydroxypropyl Methylcellulose," J. of Applied Polymer Science, Vol. 24, 1073–1087 (1979).

It is known that the addition of salts to methylcellulose can adjust its liquid-to-gel transition temperature; however, the amount of salt required to adjust the transition temperature to the physiologic temperature range often results in hyperosmotic compositions which are irritating. It is also known that the gelation temperature of methylcellulose may be altered by adding hydroxypropyl substituents, but the reported change does not bring the gelation temperature any closer to physiologic temperatures. N. Sarkar, J. of Applied Polymer Science, Vol. 24, 1084 (1979).

One effort to utilize cellulose polysaccharides in liquid pharmaceutical drug delivery vehicles is disclosed in PCT Application Publication No. WO 92/09307. This reference discloses gelable carrier compositions containing a water-soluble, nonionic cellulose ether, such as ethylhydroxyethylcellulose, and a charged surfactant. The reference gels are formed by strong hydrophobic interaction between the polymer and the charged surfactant. However, charged surfactants may be toxic if delivered to sensitive parts of the body, such as the eye. Additionally, other adjuvants may detrimentally influence the polymer-charged surfactant gelation.

Various drug delivery systems employing combinations of two types of gelling polymers have also been disclosed. U.S. Pat. No. 5,077,033 discloses a thermally irreversible gel system comprising a combination of polyoxyalkylene and ionic polysaccharides. U.S. Pat. No. 5,296,228 discloses aqueous reversibly gelling polymeric solutions containing ion exchange resin particles. The polymeric component of the solution may be a pH sensitive polymer, a temperature sensitive polymer, or combinations of both pH-sensitive polymers and temperature sensitive polymers. U.S. Pat. No. 5,252,318 also discloses reversibly gelling aqueous compositions containing combinations of polymers, in this case at least one pH-sensitive reversibly gelling polymer and at least one temperature sensitive reversibly gelling polymer. One disadvantage common to systems which require pH changes in order to gel is that they must be administered at a relatively low pH, typically in the range of 2.5–4.5. Systems administered to the eye at such a relatively low pH are irritating.

SUMMARY OF THE INVENTION

The present invention is directed toward non-toxic, non-irritating drug delivery vehicles which reversibly increase in either loss modulus or storage modulus, or both, by at least the smaller of 10 Pa or 100%, upon contact with the eye, skin, mucous membrane or a body cavity. In one embodiment, these drug delivery vehicles are administrable as a drop and, upon instillation in the eye, thicken to form a gel, whereby the residence or contact time of the delivered drugs with ocular tissue is increased. The vehicles do not require a charged surfactant or a pH-sensitive polymer in order for such increase in loss modulus or storage modulus, or both, upon instillation. The drug delivery vehicles of the present invention comprise nonionic cellulose ethers. The nonionic cellulose ethers have a molecular weight no less than 30 kD and are substituted with one or more groups selected from alkyl, hydroxyalkyl and phenyl groups such that:

$$2.2 \leq \sum_{n=1}^{N} \{n \cdot Q(n) \cdot [MS(R_n) + MS(R_nO)] -$$

$$P_N \cdot MS(R_nO)\} + Q_\phi \cdot MS(\phi) \leq 3.8$$

wherein n=substituent carbon chain length;
N=maximum value of n, $\leq 22$;
$R_n$=alkyl group of chain length n;
$R_nO$=alkoxy group of chain length n;
MS($R_n$)=MS of $R_n$;
MS($R_nO$)=MS of $R_nO$;
MS($\Phi$)=MS of phenyl groups;
Q(n)=0.837+0.155*n+0.0075*$n^2$±0.15;
$P_N$=4.4 if N$\leq$3; 4.4–1.82 if 3<N<10; and 1.82 if N$\geq$10; and
$Q_\Phi$=2.0 to 3.5.

DETAILED DESCRIPTION OF THE INVENTION

As used herein "gel" means the state of matter in which (1) G' is greater than G" (measured at a frequency in the range 0.1 to 2 Hz) when G* is greater than 10 Pa, or (2) G' is greater than or equal to twice G". G' is a storage modulus measuring the elasticity of a material, G" is a loss modulus measuring the viscous drag of a flowing liquid, and G* is a complex modulus.

As used herein "gelation temperature" means the minimum temperature at which the above definition of a gel is satisfied.

As used herein "molar substitution" or "MS" means the average number of specified substituent structural units, attached either directly or indirectly, per anhydroglucose unit comprising the cellulose backbone. The anhydroglucose unit of cellulose contains 3 pendant hydroxyl groups that can be substituted. The maximum number of substitutions is three for any substituent which is self-terminating, an example of which is an n-alkyl substituent. For substituents that are not self-terminating, such as hydroxyalkyl groups whose OH group can be further substituted, additional substituents can be concatenated and, thus, MS can excess three.

When formulated for topical administration to the eye, the drug delivery vehicles of the present invention have an osmolality of about 350 mOsm or less. Compositions having an osmolality greater than about 350 mOsm are hypertonic and can be irritating when topically administered to the eye.

When contacted with the eye, skin, mucous membrane or a body cavity, the vehicles of the present invention reversibly increase in either loss modulus or storage modulus, or both, by at least the smaller of 10 Pa or 100% in response to an increase in temperature. The vehicles of the present invention comprise one or more nonionic cellulose ethers having a molecular weight no less than 30 kD. The cellulose ethers are substituted with one or more groups selected from alkyl, hydroxyalkyl or phenyl groups such that:

$$2.2 \leq \sum_{n=1}^{N} \{n \cdot Q(n) \cdot [MS(R_n) + MS(R_nO)] -$$

-continued $$P_N \cdot MS(R_nO)\} + Q_\phi \cdot MS(\phi) \leq 3.8$$

wherein, n=substituent carbon chain length;
N=maximum value of n, $\leq 22$;
$R_n$=alkyl group of chain length n;
$R_nO$=alkoxy group of chain length n;
MS($R_n$)=MS of $R_n$;
MS($R_nO$)=MS of $PR_nO$;
MS($\Phi$)=MS of phenyl groups;
Q(n)=0.837+0.155*n+0.0075*$n^2$±0.15;
$P_N$=4.4 if N$\leq$3; 4.4–1.82 if 3<N<10; and 1.82 if N$\geq$10; and
$Q_\Phi$=2.0 to 3.5.

Let the structure function "SF" be defined as $$SF = \sum_{n=1}^{N} \{n \cdot Q(n) \cdot [MS(R_n) + MS(R_nO)] -$$

$$P_N \cdot MS(R_nO)\} + Q_\phi \cdot MS(\phi)$$

so that SF=SF {N, Q(n), $P_N$, $Q_\Phi$,MS($R_n$), MS($R_nO$), MS($\Phi$)}, an expression which registers the cumulative sum over the set {n} of hydrophilic and hydrophobic interactions produced by the amount and type of each chemical functionality. Alkyl and phenyl substituents contribute to the total hydrophobicity of a cellulose ether derivative, as does the alkyl portion of any hydroxy alkyl substituent. The hydroxy and additional ether portions of hydroxy alkyl substituents contribute to the derivative's hydrophilicity. The hydrophobic or hydrophilic contribution of a particular substituent is directly proportional to its MS, and is a function of its carbon chain length. The relative contributions of the different types of substituents are represented by the coefficients, Q and P.

To determine whether a particular substituted cellulose ether satisfies the above criteria, evaluate the function for the values of the parameters describing that cellulose ether derivative, and determine whether the SF value satisfies the above inequality.

Preferably, N$\leq$4. Also preferred are SF values such that 2.5 $\leq$SF $\leq$3.3. Most preferred are SF values such that 2.7 $\leq$SF $\leq$3.3.

The cellulose ethers useful in the present invention can be synthesized by methods known in the art, and many hydrophobically modified cellulose ether derivatives are commercially available.

The gelation of the cellulose ether-containing vehicles or formulations of the present invention occurs upon increased association of hydrophobic groups on increasing temperature. The gelation temperature of the cellulose polymer will depend upon the type, and the degree of hydrophobic and hydrophilic substitutions. For example, the gelation temperature will decrease with increase in the alkyl chain length of substituents and with increase in the molar substitution of alkyl groups. A balance of hydrophilicity is required in order to avoid precipitation.

Preferably, the cellulose ether is substituted with one or more groups selected from the group consisting of alkyl and hydroxy alkyl groups. Two examples of such cellulose ethers are methylalkylcelluloses and ethylhydroxyalkylcelluloses.

A preferred methylalkylcellulose is methylethylcellulose, wherein the methyl MS is 0.1 to 1.0, and the ethyl MS is 0.5 to 1.4. More preferred for methylethylcellulose is a methyl MS of 0.3 to 0.8 and an ethyl MS of 0.7 to 1.2. Most preferred is a methyl MS of about 0.34 and an ethyl MS of about 1.0.

Another preferred methylethylcellulose has a total MS greater than 1.6, and wherein the methyl MS is 1.3 to 2.4 and the ethyl MS is 0.1 to 0.5.

A preferred ethylhydroxyalkylcellulose is ethylhydroxyethylcellulose having an ethyl MS greater than 1 and a hydroxyethyl MS greater than 0.1. More preferred are ethylhydroxyethylcelluloses wherein the ethyl MS is 1.0 to 2.0, and the hydroxyethyl MS is 0.1 to 1.4. Most preferred are ethylhydroxyethylcelluloses wherein the ethyl MS is 1.4 to 2.0, and the hydroxyethyl MS is 0.6 to 1.4

In some cases where the gelation temperature is about 40° C. or less, it can be reduced to about 35° C. or less by adding adjuvants such as salts, charged surfactants and nonionic tonicity agents. However, in the case of ophthalmic formulations, the amount of adjuvant should be such that osmolality of the polymer-adjuvant formulation is not greater than 350 mOsm; the solution will become hypertonic above this value for ophthalmic applications. In general, the gelation temperature can be manipulated by the addition of electrolytes which are known to either salt in or salt out organic solutes. The ability of an electrolyte to salt out a polymer from its solution generally follows the order in the Hofmeister series. The common anions follow the order $I^-<Br^-<NO_3^-<Cl^-<$tartrate $<SO_4^{2-}<PO_4^{3-}$. Salts useful in the present invention include those where the anion is one or more of the following: $I^-$, $Br^-$, $NO_3^-$, $Cl^-$, tartrate, $HCO_3^-$, $CO_3^{2-}$, $SO_4^{2-}$, $PO_4^{3-}$, $B_4O_7^{2-}$, $HPO_4^{2-}$, $HPO_4^-$, titrate; and those where the cation is one or more of the following: $Na^+$, $K^+$, $Ca^{2+}$, $Al^{3+}$, $NH^{4+}$. Preferred salts for use with the vehicles of the present invention are those that contain an anion selected from the group consisting of $Cl^-$, $PO_4^-$, $HCO_3^-$, $CO_3^-$, $HPO_4^-$, and $B_4O_7^{2-}$. Most preferred for use in formulations of ethylhydroxyethylcelluloses is a combination of mono- and dibasic phosphate salts such that the vehicle contains up to 1.5 wt. % dibasic phosphate salts and 0.5 wt. % monobasic phosphate salts.

In some cases where the gelation temperature is about 40° C. or less, it can also be reduced to about 35° C. or less by the addition of a nonionic tonicity agent, such as mannitol.

A preferred example of a cellulose ether whose gelation temperature can be slightly adjusted with a salt is ethylhydroxyethylcellulose with an ethyl MS of 1.7 and a hydroxyethyl MS of 1.0. As mentioned above, the preferred inorganic salt for use in the vehicles of the present invention which contain such an ethylhydroxyethylcellulose is a combination of mono- and dibasic phosphate salts such that the vehicle contains up to 1.5 wt. % dibasic phosphate salts and 0.5 wt. % monobasic phosphate salts.

In some cases, it may be desirable to adjust upward the gelation temperature of one of the vehicles of the present invention. Such an adjustment can also be made by adding an appropriate amount of organic ions, such as tetraalkylammonium ions, known to salt in an organic solute.

For the sake of clarity and for ease of reference in the discussion below, "pre-dosed" refers to a formulation's characteristics before instillation in the eye, or in in vitro solutions mimicking this state, and "post-dosed" refers to a formulation's characteristics after instillation in the eye, or in in vitro solutions mimicking this state.

Compositions comprising the drug delivery vehicles of the present invention and one or more pharmaceutical or therapeutic agents ("drugs") are within the scope of the present invention. Such compositions may be formulated in many ways. For example, the compositions may be formulated as solutions, suspensions or weak gels which are administrable as a drop from a DROPTAINER®. Alternatively, the compositions of the present invention may be administered to the eye, skin, mucous membrane or a body cavity as an extrudable gel, which, for example, could be administered out of a tube or as a gel ribbon. Upon administration to the eye, skin, mucous membrane or a body cavity, the compositions of the present invention preferably increase in either loss modulus or storage modulus, or both, by at least the smaller of 10 Pa or 100%.

In a particularly preferred embodiment, the compositions of the present invention are administered to the eye as a drop which gels upon instillation. Preferably, the gel has a G* value from 5–1,000 Pa and, more preferably from 10–200 Pa.

Remarkably strong gels can be formed by the drug delivery vehicles of the present invention. In some embodiments, the gel formed is so strong that at least 50% of an initial amount of 20–50 mg of the gel remains undissolved in a static artificial tear solution after two hours. In other embodiments, the gel may persist longer than 24 hours.

In the embodiment of the present invention where the composition is administrable as a weak gel, the post-dosed gel preferably has a G* value from 50–100,000 Pa, and more preferably from 100–20,000 Pa.

Because the vehicles of the present invention do not rely on any pH-sensitive adjuvant for their increase in loss or storage modulus, they are preferably formulated at a pre-dosed pH from 5.0 to 8.5, such that they are not irritating when administered to the eye.

The pre-dosed temperature of the compositions of the present invention is preferably less than 30° C., and more preferably 25° C. or less.

Additionally, drug carrier substrates ("DCS") such as those defined in U.S. Pat. No. 5,212,162 may also be utilized in the drug delivery vehicles of the present invention. The entire contents of U.S. Pat. No. 5,212,162 are hereby incorporated by reference in the present specification. In addition, as used herein, "DCS" includes insoluble drug particles which may themselves act as drug carders. Preferably, the DCS will have an average particle size less than 50 microns and will be selected from the group consisting of cation exchange resins, anion exchange resins, encapsulating microspheres, insoluble drug particles, gel particles and polymeric drug complexes.

Suitable ophthalmic agents which can be included in the compositions of the present invention and administered via the method of the present invention include, but are not limited to: glaucoma agents, such as betaxolol, pilocarpine and carbonic anhydrase inhibitors; dopaminergic agonists; post-surgical antihypertensive agents, such as para-amino clonidine (apraclonidine); anti-infectives, such as ciprofloxacin; antimicrobials, such as cephalosporins and quinolones; non-steroidal and steroidal anti-inflammatories, such as suprofen, ketorolac and tetrahydrocortisol; prostaglandins; proteins; growth factors, such as EGF; immunosuppressant agents, and anti-allergics. The cellulose ether polymers of the present invention are non-ionic and thus will not interfere with charged drug compounds. Compositions of the present invention may also include combinations of ophthalmic agents. In a formulation without the use of ophthalmic agents, the present invention may also serve to supplement tears in the prevention or treatment of dry eye.

In addition to the cellulose ether and a pharmaceutical and/or therapeutic agent, the compositions of the present invention may include other components. For example, phamaceutically acceptable buffers, preservatives, nonionic surfactants, solubilizing agents, stabilizing agents, emollients, lubricants and/or tonicity agents may be included. Preferred preservatives for use in the compositions of the present invention which are formulated for local administration to the eye include alkylammoniumphenyl halides, such as benzalkonium chloride and benzalkonium bromide, and Polyquad®. Preferably in the case of ophthalmic formulations, the amount of the preservative is no more than 0.012 wt. %.

The amount of cellulose ether required will vary with the desired "post-dose" properties. Preferably, the vehicles of the present invention contain from 1 to about 10 wt. %, more preferably no more than 5 wt. %, and most preferably no more than 3 wt. %, of a cellulose ether.

The following examples are presented to illustrate further various aspects of the present invention, but are not intended to limit the scope of the invention in any Determination of viscoelastic properties of cellulose ether solutions and gels:

A dynamic mechanical thermal analyser (DMTA) (Polymer Laboratories) was used to measure the viscoelastic properties of nonionic cellulose ether solutions and gels. This DMTA consists of a mechanical spectrometer head, the dynamic control system (analyser), and a temperature controller. The mechanical spectrometer head used for the viscoelastic measurement was torsion type. The torsion head allows the viscoelastic properties of solid and liquid samples to be studied using small amplitude sinusoidally oscillating shear.

A dual cylindrical cavity Couette cell was used. The top cylinder was attached to the upper (vibrating) damp and the bottom concentric cylinders were attached to the lower fixed damp. Two cavities were formed; one between the inner bottom cylinder and the top cylinder, and the other between the outer bottom cylinder and the top cylinder. The height, outside diameter and inside diameter of the top cylinder were 57.02 mm, 34.01 mm, and 32.01 mm, respectively. The height, outside diameter and inside diameter of the inner bottom cylinder were 51.96 mm, 28.14 mm, and 26.02 mm, respectively. The height, outside diameter and inside diameter of the outer bottom cylinder were 64.94 mm, 40.03 mm, and 37.89 mm, respectively. The gap between the inner and outer bottom cylinders was filled with the sample up to the height of the inner cylinder. This gap is completely filled with about 21 g of the sample. The geometric constant, K required for the correct calculation of shear modulus of the sample for the dual cavity Couette cell is given by the following formula:

$$K = K_{inner\ cavity} + K_{outer\ cavity}$$

$$K_{inner\ cavity} = (4\pi d r_1^2 r_2^2)(r_2^2 - r_1^2)$$

where:
- $r_1$: Outside radius of the bottom inner cylinder,
- $r_2$: Inside radius of the top cylinder,
- I: Height of the solution; and $$K_{outer\ cavity} = (4\pi d r_3^2)(r_4^2 - r_3^2)$$

where:
- $r_3$: Outside radius of the top cylinder,
- $r_4$: Inside radius of the bottom outer cylinder,
- I: Height of solution in the cylinder.

All the calculations are done in meters and the value of log (K) is −2.812 for the above mentioned dimensions.

All the measurements were carried out at a frequency of 1 Hz and a strain of X1(peak to peak displacement of 23 microns). The pre-dose viscoelastic measurements were carried out at 25° C., then the sample was heated to 35° C. at a rate of 0.5–1° C./min. The post-dose viscoelastic measurements were carried out at 35° C. DMTA provides storage shear modulus (elasticity) G' and loss tangent tan δ. The loss shear modulus G" and the complex shear modulus G* were calculated from G' and tan δ. The DMTA precision in the measurements of the G' and G" values reported in the examples below is approximately ±4 Pa.

EXAMPLES

EXAMPLE 1

A solution was prepared of 3 wt. % methylethylcellulose (MS of ethyl groups=1.0, MS of methyl groups=0.34) in deionized water. This solution was stirred in an ice bath for about two hours to completely hydrate the polymer; on complete hydration the solution became dear (or translucent if not completely dear). The solution was then left at room temperature. The osmolality of this solution was approximately 13 mOsm. To measure its viscoelastic properties in pre-dose (25° C.) and post-dose (35° C.) states, the sample was cooled in an ice bath and then about 21–22 g of it were poured in the Couette cell. The Couette cell was equilibrated to room temperature for about 10 minutes. Then the viscoelastic measurements were carried out using the DMTA. The measurements were carried out at 25° C. for 30 minutes followed by a ramp from 25° to 35° C. at a rate of 1° C./min and followed by an isotherm at 35° C. for 60 minutes. At the end of the isotherm at 25° C., G', G", and G* values were about 15 Pa, 5 Pa, and 16 Pa, respectively. At the end of the isotherm at 35° C., G', G", and G* values were about 71 Pa, 6 Pa, and 72 Pa, respectively. Thus, the storage modulus of this sample increased by more than 50 Pa simply by raising the temperature from 25° to 35° C.

The cellulose ether of this Example contains only two functional groups and both are simple alkyl groups, methyl (with n=1) and ethyl (with n=2). The maximum chain length is derived from the ethyl substitution, so that N=2. This cellulose ether contains neither phenyl nor alkoxy groups, thus they contribute nothing to the sum. From the definitions above Q(1)=1 and Q(2)=1.3.

Symbolically, for this Example SF{N, Q(n), $P_N$, $Q_{101}$, MS($R_n$), MS($R_n$O), MS(Φ)}=SF{N=2, Q(1)=1.0, Q(2)=1.3, MS($R_1$)=0.34, MS($R_2$)=1.00, MS($R_n$O)=0, MS(Φ)=0}= 2.94.

EXAMPLE 2

A solution was prepared of 3.5 wt. % methylethylcellulose (MS of ethyl groups=1.0, MS of methyl groups=0.34) in deionized water. This solution was stirred in an ice bath for about two hours to completely hydrate the polymer. The solution was then left at room temperature. The osmolality of this solution was approximately 15 mOsm. To measure its viscoelastic properties in pre-dose (25° C.) and pest-dose (35° C.) states, the sample was cooled in an ice bath and then about 21–22 g of it were poured in the Couette cell. The Couette cell was equilibrated to room temperature for about 10 minutes. Then the viscoelastic measurements were carried out using the DMTA. The measurements were carried out at 25° C. for 30 minutes followed by a ramp from 25° to 35° C. at a rate of 1° C./min and followed by an isotherm at 35° C. for 60 minutes. At the end of the isotherm at 25° C., G', G", and G* values were about 28 Pa, 6 Pa, and 28 Pa, respectively. At the end of the isotherm at 35° C., G', G", and G* values were about 133 Pa, 7 Pa, and 133 Pa, respectively. Thus, the storage modulus of this sample increased by more than 100 Pa simply by raising the temperature from 25° to 35° C.

EXAMPLE 3

A solution was prepared of 2.5 wt. % methylethylcellulose (MS of ethyl groups=1.0, MS of methyl groups=0.34), 0.2 wt. % dibasic sodium phosphate anhydrous, 0.04 wt. % monobasic sodium phosphate monohydrate, and 3.6 wt. % mannitol in deionized water. This solution was stirred in an ice bath for about two hours to completely hydrate the polymer. The solution was then left at room temperature. The osmolality of this solution was approximately 301 mOsm and the pH of this solution was about 7.2. To measure its viscoelastic properties in pre-dose (25° C.) and post-dose (35° C.) states, the sample was cooled in an ice bath and then about 21–22 g of it were poured in the Couette cell. The Couette cell was equilibrated to room temperature for about 10 minutes. Then the viscoelastic measurements were carried out using the DMTA. The measurements were carried out at 25° C. for 30 minutes followed by a ramp from 25° to 35° C. at a rate of 1° C./min and followed by an isotherm at 35° C. for 60 minutes. At the end of the isotherm at 25° C., G', G", and G* values were about 20 Pa, 6 Pa, and 21 Pa, respectively. At the end of the isotherm at 35° C., G', G", and G* values were about 143 Pa, 13 Pa, and 144 Pa, respectively. Thus, the storage modulus of this sample increased by more than 120 Pa simply by raising the temperature from 25° to 35° C.

EXAMPLE 4

A solution was prepared of 2.5 wt. % methylethylcellulose (MS of ethyl groups=1.0, MS of methyl groups=0.34), 0.2 wt. % dibasic sodium phosphate anhydrous, 0.035 wt. % monobasic sodium phosphate monohydrate, 3.1 wt. % mannitol, and 0.01% benzalkonium chloride in deionized water. This solution was stirred in an ice bath for about two hours to completely hydrate the polymer. The solution was then left at room temperature. The osmolality of this solution was approximately 290 mOsm and the pH of this solution was about 7.2. To measure its viscoelastic properties in pre-dose (25° C.) and post-dose (35° C.) states, the sample was cooled in an ice bath and then about 21–22 g of it were poured in the Couette cell. The Couette cell was equilibrated to room temperature for about 10 minutes. Then the viscoelastic measurements were carried out using the DMTA. The measurements were carried out at 25° C. for 30 minutes followed by a ramp from 25° to 35° C. at a rate of 1° C./min and followed by an isotherm at 35° C. for 60 minutes. At the end of the isotherm at 25° C., G', G", and G* values were about 20 Pa, 7 Pa, and 21 Pa, respectively. At the end of the isotherm at 35° C., G', G", and G* values were about 84 Pa, 8 Pa, and 85 Pa, respectively. Thus, the storage modulus of this sample increased only by about 64 Pa upon an increase in temperature from 25° to 35° C. In contrast to this sample, the storage modulus of the solution in Example 3, similar to this Example 4 but which did not contain any benzalkonium chloride, increased by about 120 Pa upon the same increase in temperature. This demonstrates that the presence of benzalkonium chloride, which is commonly used as a preservative and which possesses some surface activity, did not enhance the storage modulus increase upon temperature increase from 25° to 35° C.

EXAMPLE 5

A solution was prepared of 3.0 wt. % ethylhydroxyethylcellulose (MS of ethyl groups=1.7, MS of hydroxyethyl groups=1.0), in deionized water. This solution was stirred in an ice bath for about two hours to completely hydrate the polymer. The solution was then left at room temperature. The osmolality of this solution was approximately about 10 mOsm. To measure its viscoelastic properties in pre-dose (25° C.) and post-dose (35° C.) states, about 21–22 g of this sample were poured in the Couette cell. Then the viscoelastic measurements were carried out using the DMTA. The measurements were carried out at 25° C. for 10 minutes followed by a ramp from 25° to 35° C. at a rate of 0.5° C./min and followed by isotherm at 35° C. for 30 minutes. This was followed by a ramp from 35° to 45° C. at a rate of 0.5° C./min and an isotherm at 45° C. for 30 minutes. At the end of the isotherm at 25° C., G', G", and G* values were about 5 Pa, 5 Pa, and 7 Pa, respectively. At the end of the isotherm at 35° C., G', G", and G* values were about 6 Pa, 5 Pa, and 7 Pa, respectively. Thus, there was no significant increase in the storage modulus or the complex shear modulus upon increasing temperature from 25° to 35° C. The 3 wt % ethylhydroxyethylcellulose solution did not gel at 35° C. However, as the temperature was increased from 35° to 45° C., a significant increase in the storage modulus was observed; the solution gelled at about 40° C. At the end of an isotherm at 45° C., G', G", and G* values were about 53 Pa, 9 Pa, and 54 Pa, respectively. Thus the storage modulus of this sample increased by about 45 Pa upon increasing temperature from 35° to 45° C.

The calculation of SF becomes somewhat more complex for cellulose ethers with multifunctional substitution. An example of such an SF is illustrated here. In this case the backbone is substituted on average with both ethyl and hydroxyethyl substituents, and no others. Thus there will be terms with but one value of n, n=2, but since there are two types of substituents with n=2, there will be both $MS(R_n)$ and $MS(R_nO)$ terms. It happens for this set of substituents, the largest alkyl group also has just two carbons, so N=2 as well. Because of the additional ether linkage, derived from the substitution of the hydroxyethyl groups, the hydrophilic correction term $P_2$ is required to diminish the effect of the hydrophobic contribution of the ethyl in the hydroxyethyl substituent. The value required for $P_2$ is 4.4.

With these values and the levels of substitution determined for this material, SF defined earlier assumes the value $$SF\{N,\ Q(n),\ P_N,\ Q_\Phi,\ MS(R_n),\ MS(R_nO),\ MS(\Phi)\} =$$

$$SF\{N = 2,\ Q(2) = 1.3,\ P_2 = 4.4,\ MS(R_2) = 1.70,$$

$$MS(R_2O) = 1.0,\ MS(\Phi) = 0\} = 2.62.$$

EXAMPLE 6

A solution was prepared of 3.0 wt. % ethylhydroxyethylcellulose (MS of ethyl groups=1.7, MS of hydroxyethyl groups=1.0), 1.3 wt. % dibasic sodium phosphate anhydrous, 0.33 wt % monobasic sodium phosphate monohydrate in deionized water. This solution was stirred in an ice bath for about two hours to completely hydrate the polymer. The solution was then left at room temperature. The osmolality of this solution was approximately 292 mOsm and the pH of this solution was about 7.3. To measure its viscoelastic properties in pre-dose (25° C.) and post-dose (35° C.) states, about 21–22 g of this sample were poured in the Couette cell. Then the viscoelastic measurements were carried out using the DMTA. The measurements were carried out at 25° C, for 10 minutes followed by a ramp from 25° to 35° C. at a rate of 0.5° C./min and followed by an isotherm at 35° C. for 60 minutes. At the end of the isotherm at 25° C., G', G", and G* values were about 5 Pa, 8 Pa, and 10 Pa, respectively. At the end of the isotherm at 35° C., G', G", and G* values were about 25 Pa, 6 Pa, and 26 Pa, respectively. Thus, in contrast to Example 5 which did not contain any salts, the solution of this Example gelled and the storage modulus increased by about 20 Pa as the temperature increased from 25° to 35° C. Thus, the gelation temperature was lowered to about 35° C. by adding salt in an amount which did not increase osmolality above 350 mOsm.

EXAMPLE 7

A solution was prepared of 2.5 wt % methylcellulose (MS of methyl groups=1.6) in hot deionized water. The polymer was hydrated by stirring this solution either in an ice bath or at room temperature. The osmolality of this solution was approximately 8 mOsm. To measure its viscoelastic properties in pre-dose (25° C.) and post-dose (35° C.) states, about 21–22 g of this sample were poured in the Couette cell. Then the viscoelastic measurements were carried out using the DMTA. The measurements were carried out at 25° C. for 10 minutes followed by a ramp from 25° to 35° C. at a rate of 0.5° C./min and followed by an isotherm at 35° C. for 30 minutes. At the end of the isotherm at 25° C., G', G", and G* values were about 4 Pa, 4 Pa, and 6 Pa, respectively. At the end of the isotherm at 35° C., G', G", and G* values were about 4 Pa, 4 Pa, and 6 Pa, respectively. Thus, upon increasing temperature from 25° to 35° C., this solution did not gel and did not show any increase in storage modulus.

For this Example, SF is simple to calculate since there are neither phenyl nor alkoxy groups and but one alkyl group, a methyl ether. The only non-zero substitution variable is $MS(1)=1.6$. Then for this Example $SF\{N, Q(n), P_N, Q_\Phi, MS(R_n), MS(R_nO), MS(\Phi)\} = SF\{N=1, Q(1)=1.0, MS(R_1)=1.6, MS(R_nO)=0, MS(\Phi)=0\}=1.6$.

EXAMPLE 8

A solution was prepared of 2.5 wt % methylcellulose (MS of methyl groups=1.6), 1.3 wt. % dibasic sodium phosphate anhydrous sodium phosphate monohydrate in deionized water. The polymer was hydrated by stirring this solution either in an ice bath or at room temperature. The osmolality of this solution was approximately 291 mOsm and the pH of this solution was 7.3. To measure its viscoelastic properties in pre-dose (25° C.) and post-dose (35° C.) states, about 21–22 g of this sample were poured in the Couette cell. Then the viscoelastic measurements were carried out using the DMTA. The measurements were carried out at 25° C. for 10 minutes followed by a ramp from 25° to 35° C. at a rate of 0.5° C. min and followed by an isotherm at 35° C. for 30 minutes. At the end of the isotherm at 25° C., G', G", and G* values were about 4 Pa, 4 Pa, and 6 Pa, respectively. At the end of the isotherm at 35° C., G', G", and G* values were about 7 Pa, 4 Pa, and 8 Pa, respectively. Thus, upon increasing temperature from 25° to 35° C., this solution did not gel and did not show a significant increase in storage modulus even though it contained an amount of phosphate salts sufficient to raise the osmolality of the solution to 293 mOsm.

EXAMPLE 9

A solution was prepared of 3 wt % methylcellulose (MS of methyl groups =1.6–1.9, Aldrich Chemicals, 2% aqueous solution has viscosity of 1500 centipoise) in hot deionized water. The polymer was hydrated by stirring this solution either in an ice bath or at room temperature. The osmolality of this solution was approximately 26 mOsm. To measure its viscoelastic properties in pre-dose (25° C.) and post-dose (35° C.) states, about 21–22 g of this sample were poured in the Couette cell. Then the viscoelastic measurements were carried out using the DMTA. The measurements were carried out at 25° C. for 10 minutes followed by a ramp from 25° to 35° C. at a rate of 0.5° C./min and followed by an isotherm at 35° C. for 30 minutes. This was followed by a ramp from 35° to 45° C. at a rate of 0.5° C./min and an isotherm at 45° C. for 30 minutes. At the end of the isotherm at 25° C., G', G", and G* values were about 10 Pa, 28 Pa, and 30 Pa, respectively. At the end of the isotherm at 35° C., G', G", and G* values were about 10 Pa, 20 Pa, and 22 Pa, respectively. At the end of the isotherm run at 45° C., G', G", and G* values were about 10 Pa, 12 Pa, and 15 Pa, respectively. Thus, this solution did not gel and did not show any increase in storage modulus even upon increasing temperature from 25° to 45° C.

For this Example, SF is simple to calculate since there are neither phenyl nor alkoxy groups and but one alkyl group, a methyl ether. The only non-zero substitution variable is $MS(1)=1.6-1.9$. Then for this Example $SF\{N, Q(n), P_N, Q_\Phi, MS(R_n), MS(R_nO), MS(\Phi)\} = SF\{N=1, Q(1)=1.0, MS(R_1)=1.6-1.9, MS(R_nO)=0, MS(\Phi)=0\}=1.6-1.9$.

EXAMPLE 10

A solution was prepared of 6 wt. % methylcellulose (MS of methyl groups=1.6–1.9, Aldrich Chemicals, 2% aqueous solution has viscosity of 15 centipoise) in hot deionized water. The polymer was hydrated by stirring this solution either in an ice bath or at room temperature. The osmolality of this solution was approximately about 55 mOsm. To measure its viscoelastic properties in pre-dose (25° C.) and postdose (35° C.) states, about 21–22 g of this sample was poured in the Couette cell. Then the viscoelastic measurements were carried out using the DMTA. The measurements were carried out at 25° C. for 10 minutes followed by a ramp from 25° to 35° C. at a rate of 0.5° C./min and followed by an isotherm at 35° C. for 30 minutes. This was followed by a ramp from 35° to 45° C. at a rate of 0.5° C./min and an isotherm at 45° C. for 30 minutes. At the end of the isotherm at 25° C., G', G", and G* values were about 6 Pa, 10 Pa, and 12 Pa, respectively. At the end of the isotherm at 35° C., G', G", and G* values were about 6 Pa, 10 Pa, and 12 Pa, respectively. At the end of the isotherm run at 45° C., G', G", and G* values were about 10 Pa, 10 Pa, and 13 Pa, respectively. Thus, this solution did not gel and did not show any increase in storage modulus even upon increasing temperature from 25° to 45° C.

We claim:

1. A nontoxic drug delivery vehicle which reversibly increases in either loss modulus or storage modulus, or both, by at least the smaller of 10 Pa or 100% in response to an increase in temperature upon contact with the eye, skin, mucous membrane or body cavity, wherein the vehicle does not require a charged surfactant or pH-sensitive polymer for such increase in either loss modulus or storage modulus, or both, and wherein the vehicle comprises a nonionic cellulose ether having a molecular weight no less than 30 kD and which is substituted with one or more substituents selected from the group consisting of alkyl, hydroxyalkyl and phenyl groups such that $$2.2 \leq \sum_{n=1}^{N} \{n \cdot Q(n) \cdot [MS(R_n) + MS(R_nO)] - P_N \cdot MS(R_nO)\} + Q_\phi \cdot MS(\phi) \leq 3.8$$

wherein, n=substituent carbon chain length;

N=maximum value of n, $\leq 22$;

$R_n$=alkyl group of chain length n;

$R_nO$=alkoxy group of chain length n;

$MS(R_n)$=MS of $R_n$;

$MS(R_nO)$=MS of $R_nO$;

$MS(\Phi)$=MS of phenyl groups;

$Q(n)=0.837+0.155*n+0.0075*n^2\pm0.15$;

$P_N$=4.4 if N $\leq$3; 4.4–1.82 if 3<N<10; and 1.82 if N$\geq$10; and $Q_\phi$=2.0 to 3.52;

provided that the nonionic cellulose ether is not a cellulose ether having only ethyl and hydroxyethyl substituents, an ethyl MS from 1.2 to 2.5 and a hydroxyethyl MS from 0.5 to 1.5, and a cloud point from 30° to 35° C. as spectrophotometrically determined for a 1.0 wt % solution of the cellulose ether in water, heated at a rate of 10° C./min.

2. The vehicle of claim 1 wherein the vehicle is an ophthalmic vehicle having an osmolality $\leq$350 mOsm.

3. The vehicle of claim 2 wherein N$\leq$4.

4. The vehicle of claim 2 wherein $$2.5 \leq \sum_{n=1}^{N} \{n \cdot Q(n) \cdot [MS(R_n) + MS(R_nO)] - P_N \cdot MS(R_nO)\} + Q_\phi \cdot MS(\phi) \leq 3.3.$$

5. The vehicle of claim 4 wherein $$2.7 \leq \sum_{n=1}^{N} \{n \cdot Q(n) \cdot [MS(R_n) + MS(R_nO)] - P_N \cdot MS(R_nO)\} + Q_\phi \cdot MS(\phi) \leq 3.3.$$

6. The vehicle of claim 2 wherein either the vehicle's loss modulus or storage modulus, or both, increases by at least 15 Pa.

7. The vehicle of claim 2 wherein the vehicle is administrable as a drop.

8. The vehicle of claim 2 wherein the vehicle is a gel prior to instillation.

9. The vehicle of claim 2 wherein the vehicle forms a gel upon instillation in the eye.

10. The vehicle of claim 9 wherein the gel has a G* value from 5–1,000 Pa.

11. The vehicle of claim 10 wherein the gel has a G* value from 10–200 Pa.

12. The vehicle of claim 9 wherein at least 50% of an initial amount of 20–50 mg of the gel remains undissolved in a static artificial tear solution after two hours.

13. The vehicle of claim 2 wherein the vehicle is administrable as an extrudable gel.

14. The vehicle of claim 13 wherein the vehicle's post-dosed G* value is from 50–100,000 Pa.

15. The vehicle of claim 14 wherein the vehicle's post-dosed G* value is from 100–20,000 Pa.

16. The vehicle of claim 2 wherein the vehicle has a pre-dosed pH from 5.0 to 8.5.

17. The vehicle of claim 2 further comprising a preservative selected from the group consisting of alkylammoniumphenyl halides and Polyquaternium 1.

18. The vehicle of claim 17 wherein the amount of preservative is not greater than 0.012 wt. %.

19. The vehicle of claim 2 wherein the amount of the cellulose ether is no more than 10 wt. %.

20. The vehicle of claim 19 wherein the amount of the cellulose ether is no more than 5 wt. %.

21. The vehicle of claim 20 wherein the amount of the cellulose ether is no more than 3 wt. %.

22. The vehicle of claim 2 further comprising a drug carrier substrate having an average particle size less than 50 μm. and selected from the group consisting of cation exchange resins, anion exchange resins, encapsulating microspheres, insoluble drug particles, gel particles and polymeric drug complexes.

23. The vehicle of claim 2 further comprising one or more drugs selected from the group consisting of anti-glaucoma agents, dopaminergic agonists, post-surgical anti-hypertensive agents, anti-infectives, nonsteroidal and steroidal anti-inflammatory agents, prostaglandins, proteins, growth factors, immunosuppresant agents, and anti-allergic agents.

24. The vehicle of claim 2 wherein the cellulose ether has a gelation temperature $\leq$40° C. and wherein the vehicle further comprises an adjuvant in an amount sufficient to lower the gelation temperature to $\leq$35° C., provided that the adjuvant is not a charged surfactant.

25. The vehicle of claim 24 wherein the adjuvant is a salt having an anion selected from the group consisting of $Cl^-$, $PO_4^-$, $HCO_3^-$, $CO_3^-$, $HPO_4^-$, and $B_4O_7^{2-}$.

26. The vehicle of claim 25 wherein the cellulose ether is an ethylhydroxyethylcellulose other than an ethylhydroxyethylcellulose having an ethyl MS from 1.2 to 2.5, an ethyl MS from 0.5. to 1.5 and a cloud point from 30° to 35° C., the salt is present in an amount less than 2 wt. %, and the salt comprises up to 1.5 wt. % dibasic phosphate salts and up to 0.5 wt. % monobasic phosphate salts.

27. The vehicle of claim 2 wherein the cellulose ether is substituted with one or more groups selected from the group consisting of alkyl and hydroxyalkyl groups.

28. The vehicle of claim 27 wherein N$\leq$4.

29. The vehicle of claim 28 wherein $$2.5 \leq \sum_{n=1}^{N} \{n \cdot Q(n) \cdot [MS(R_n) + MS(R_nO)] - P_N \cdot MS(R_nO)\} + Q_\phi \cdot MS(\phi) \leq 3.3.$$

30. The vehicle of claim 29 wherein $$2.7 \leq \sum_{n=1}^{N} \{n \cdot Q(n) \cdot [MS(R_n) + MS(R_nO)] - P_N \cdot MS(R_nO)\} + Q_\phi \cdot MS(\phi) \leq 3.3.$$

31. The vehicle of claim 27 wherein the cellulose ether is methylalkylcellulose.

32. The vehicle of claim 31 wherein the methylalkylcellulose is methylethylcellulose.

33. The vehicle of claim 32 wherein the total MS is greater than 1.6, and wherein the methyl MS is 1.3 to 2.4 and the ethyl MS is 0.1 to 0.5.

34. The vehicle of claim 27 wherein the cellulose ether is an ethylhydroxyethylcellulose having an ethyl MS greater than 1 and a hydroxyethyl MS greater than 0.1, provided that the ethylhydroxyethylcellulose is not an ethylhydroxyethylcellulose having an ethyl MS from 1.2 to 2.5, an ethyl MS from 0.5 to 1.5 and a cloud point from 30° to 35° C.

35. A nontoxic ophthalmic drug delivery vehicle which reversibly increases in either loss modulus or storage modulus, or both, by at least the smaller of 10 Pa or 100% in response to an increase in temperature upon instillation in the eye, wherein the vehicle has an osmolality $\leq$350 mOsm and does not require a charged surfactant or pH-sensitive polymer for such increase in either loss modulus or storage modulus, or both, and wherein the vehicle comprises methylethylcellulose having a molecular weight no less than 30 kD, a methyl MS from 0.1 to 1.0, and an ethyl MS from 0.5 to 1.4.

36. The vehicle of claim 35 wherein the methyl MS is 0.3 to 0.8 and the ethyl MS is 0.7 to 1.2.

37. The vehicle of claim 36 wherein the methyl MS is about 0.34 and the ethyl MS is about 1.0.

38. A nontoxic ophthalmic drug delivery vehicle which gels in response to an increase in temperature upon instillation in the eye, wherein the vehicle has an osmolality $\leq 350$ mOsm and does not require a charged surfactant or pH-sensitive polymer in order to gel, and wherein the vehicle comprises ethylhydroxyethylcellulose having a molecular weight no less than 30 kD, an ethyl MS from 1.0 to 2.0, and an hydroxyethyl MS from 0.1 to 1.4, and an adjuvant in an amount sufficient to lower the gelation temperature of the vehicle to $\leq 35°$ C., provided that the adjuvant is not a charged surfactant.

39. The vehicle of claim 38 wherein the ethyl MS is from 1.4 to 2.0 and the hydroxyethyl MS is from 0.6 to 1.4.

* * * * *